United States Patent [19]
Homann et al.

[11] Patent Number: 6,133,001
[45] Date of Patent: Oct. 17, 2000

[54] STEREOSELECTIVE MICROBIAL REDUCTION FOR THE PREPARATION OF 1-(4-FLUOROPHENYL)-3(R)-[3(S)-HYDROXY-3-(4-FLUOROPHENYL)PROPYL)]-4(S)-(4-HYDROXYPHENYL)-2-AZETIDINONE

[75] Inventors: Michael J. Homann, Clinton; Edward Previte, N. Brunswick, both of N.J.

[73] Assignee: Schering Corporation, Kenilworth, N.J.

[21] Appl. No.: 09/256,029

[22] Filed: Feb. 23, 1999

Related U.S. Application Data

[60] Provisional application No. 60/075,499, Feb. 23, 1998.
[51] Int. Cl.⁷ .................................................. C12P 17/10
[52] U.S. Cl. ............................................ 435/121; 435/280
[58] Field of Search ..................... 435/280, 121

[56] References Cited

U.S. PATENT DOCUMENTS

| | | | |
|---|---|---|---|
| 5,618,707 | 4/1997 | Homann et al. | 435/146 |
| 5,767,115 | 6/1998 | Rosenblaum et al. | 514/210 |

FOREIGN PATENT DOCUMENTS

| | | | |
|---|---|---|---|
| 61-141894 | 6/1986 | Japan . | |
| WO 95/08532 | 3/1995 | WIPO . | |
| WO 97/16424 | 5/1997 | WIPO . | |

OTHER PUBLICATIONS

Derwent Abstract 86–208964 of JP61141894.
Santaniello et al, *Chem. Rev.*, 92(1992), p. 1071–1087.
Belan et al, J. Org. Chem., 52 (1987), p. 256–260.

*Primary Examiner*—Sandra E. Saucier
*Attorney, Agent, or Firm*—Anita W. Magatti

[57] ABSTRACT

A process for the stereoselective microbial reduction of compound of formula II to compound of formula I

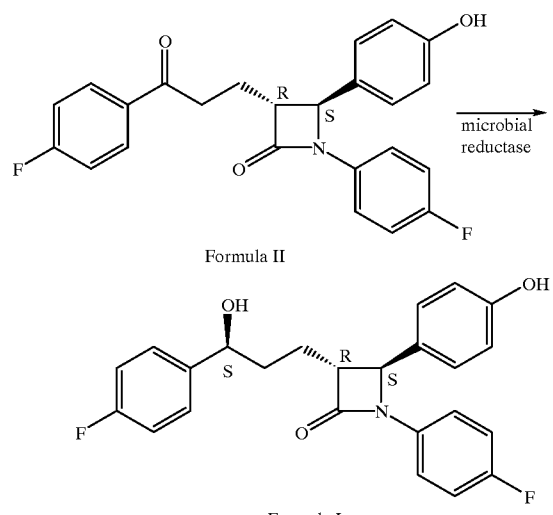

comprising adding compound of formula II to a medium, medium and buffer, medium and solvent, or medium and a mixture of buffer and solvent containing a microorganism, preferably *Rhodococcus fascians* ATCC No. 202210 or fungal isolate *Geotrichum candidum* ATCC No. 74487, incubating the resulting mixture, and isolating a hydroxy compound of formula I, is described. The compound of formula I is a serum cholesterol lowering agent.

5 Claims, No Drawings

STEREOSELECTIVE MICROBIAL REDUCTION FOR THE PREPARATION OF 1-(4-FLUOROPHENYL)-3(R)-[3(S)-HYDROXY-3-(4-FLUOROPHENYL)PROPYL)]-4(S)-(4-HYDROXYPHENYL)-2-AZETIDINONE

This application claims benefit of Provisional appl. Ser. No. 60/075,499 filed Feb. 23, 1998.

BACKGROUND OF THE INVENTION 1-(4-Fluorophenyl)-3(R) -[3(S)-hydroxy-3-(4-fluorophenyl)-propyl)]-4(S)-(4-hydroxyphenyl)-2-azetidinone is disclosed as a cholesterol lowering agent in WO 95/08532, published Mar. 30, 1995. U.S. Pat. No. 5,618,707 discloses stereoselective microbial reduction of a keto intermediate (4-(4-fluoro-benzoyl)butyric acid or a phenyloxazolidinone conjugate thereof) used in the preparation of the azetidinone to the corresponding hydroxy intermediate using the microorganism *Zygosaccharomyces balili* or *Schizosaccharomyces octosporus*.

SUMMARY OF THE INVENTION

The present invention relates to a process for the microbiological reduction of carbonyl groups which comprises the use of microorganisms (obtained from environmental sources and culture collections, e.g., the American Type Culture Collection (ATCC)) in medium, medium and buffer, medium and solvent, or medium and a mixture of buffer and solvent to which a ketone compound can be added so that a compound having a hydroxy group of desired stereochemistry can be formed, accumulated and isolated.

In particular, the present invention relates to a process for the stereoselective reduction of 1-(4-fluorophenyl)-3(R)-[3-oxo-3-(4-fluorophenyl)propyl)]-4(S)-(4-hydroxyphenyl)-2-azetidinone to 1-(4-fluorophenyl)- 3(R) -[3(S)-hydroxy-3-(4-fluorophenyl)-propyl)]-4(S)-(4-hydroxyphenyl)-2-azetidinone comprising adding 1-(4-fluoro-phenyl)-3(R)-[3-oxo-3-(4-fluorophenyl)-propyl))-4(S)-(4-hydroxyphenyl)-2-azetidinone to a micoorganism in medium, medium and buffer, medium and solvent, or medium and a mixture of buffer and solvent, incubating the resulting mixture, and isolating 1-(4-fluoro-phenyl)-3(R) -[3(S)-hydroxy-3-(4-fluorophenyl)-propyl)]-4(S)-(4-hydroxyphenyl)-2-azetidinone.

Microorganisms selected from the group consisting of the following genera have been found to be useful in the reduction of this invention: Aspergillus, Curvularia, Doratomyces, Geotrichum, Mortierella, Mucor, Saccharomyces, Scytalidium, Pichia, Torulaspora, Neurospora and Rhodococcus. The following species of the above genera are preferred: *Aspergillus niveus, Curvularia lunata, Doratomyces stemonitis, Geotrichum candidum, Mortierella isabellina, Mucor racemosus* and *circinelloides, Saccharomyces cerevisiae* and *uvarum, Scytalidium lignicola, Pichia methanolitica, Torulaspora fermentati* and species, *Neurospora crassa* and *Rhodococcus elythropolis, fascians, rhodochrous* and species.

In particular, the present invention relates to a process for the microbiological reduction of the carbonyl group of 1-(4-fluorophenyl)-3(R)-[3-oxo-3-(4-fluorophenyl) propyl)]-4(S)-(4-hydroxyphenyl)-2-azetidinone (Formula II, below) comprising adding said compound to a microorganism in medium, medium and buffer, medium and solvent, or medium and a mixture of buffer and solvent, especially wherein the microorganism is Rhodococcus fascians ATCC No. 202210 or fungal isolate *Geotrichum candidum* ATCC No. 74487, incubating the resulting mixture, and isolating 1-(4-fluorophenyl)-3(R)-[3(S)-hydroxy-3-(4-fluorophenyl)-propyl)]-4(S)-(4-hydroxyphenyl)-2-azetidinone (Formula I, below).

A viable culture of the fungal isolate has been deposited Feb. 24, 1999, in the collection of the American Type Culture Collection, 10801 University Boulevard, Manassas, Va. 20110-2209, where the fungal isolate has been assigned accession number ATCC 74487. Should the depositied culture become lost, destroyed or non-viable during the longer of the thirty (30) year period from the date the culture was deposited or the five (5) year period after the last request for the deposited culture or the effective life of the patent which issues from this application, the culture will be replaced, upon notice, by applicants or assignee(s) of this application. Subcultures of Geotrichum candidum ATCC 74487 are available during the pendency of this application to one determined by the Commissioner of Patents and Trademarks to be entitled thereto under 37 C.F.R. 1.14 and 35 U.S.C. 122 and will be available to the public without restriction once a patent based on this application is granted. Use of the fungal isolate is dependent on the U.S. Patent Laws. *Rhodococcus fascians* ATCC No. 202210 is available from the ATCC under the same conditions.

DETAILED DESCRIPTION

This invention relates to a method for performing the following stereospecific reduction using a microorganism.

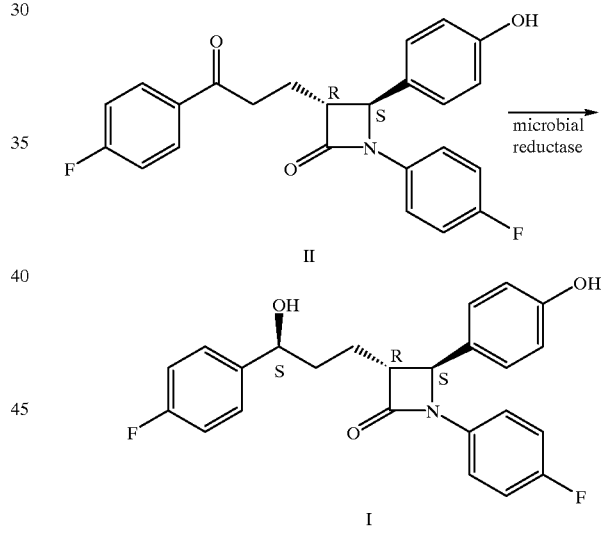

The microbiological reduction is carried out by adding the ketone substrate of formula II, above, to medium, medium and buffer, medium and solvent, or medium and a mixture of buffer and solvent containing microorganisms. The incubation may be conducted at temperatures in the range from between about 20° C. and about 40° C., preferably 30° C., while adjusting the initial pH value of the reaction in the range from between about 5.0 and about 9.0, preferably 7.0.

The initial concentration of compound II in the reaction may vary from between about 0.5 g/l and about 10.0 g/l, and is preferably 2–4.0 g/l.

Suitable fermentation media, buffers and solvents are known to those skilled in the art. Fermentation media typically contain a carbon and nitrogen source or mixtures thereof, using such ingredients as yeast extract, nutrient broth, dextrose (cerelose), white potato dextrin, soy flour, peptone and other components known in the art. Typical buffers are phosphate buffer (e.g., 0.1M at pH 7), MES (2-[N-morpholino]ethane-sulfonic acid), Bis-Tris (bis[2-hydroxyethyl]iminotris[hydroxymethyl]-methane), PIPES (1,4-piperazine-diethanesulfonic acid), HEPES (N-[2-hydroxyethyl]piperazine-N'-[2-ethanesulfonic acid]), TRIS (tris(hydroxymethyl)aminomethane) and MOPS (3-[N-morpholino]propanesulfonic acid) buffer (e.g., 0.1M at pH 7). Typical solvents are acetonitrile, acetone, ethyl ether, isopropanol, t-butanol, isoamyl alcohol, p-dioxane, isopropyl ether, dimethyl sulfoxide, t-butyl methyl ether (TBME), toluene, tetrahydrofuran and $CH_2Cl_2$. Preferably, the microbial reduction is carried out in fermentation media.

The duration of the chiral reduction reaction may vary from about 18 to about 96 hours, and is preferably about 48–72 hours.

At the end of the reduction reaction, the hydroxy compound of formula I may be extracted by well known methods, using organic solvents such as ethyl acetate (EtOAc), t-butyl methyl ether (TBME), methylene chloride ($CH_2Cl_2$) and the like. Adsorption to resins, chromatography, and other physical methods known to the art may also be used to extract the hydroxy compound of formula I.

A large number of microorganisms were investigated to determine whether or not they reduce the ketone compound of formula II. Many such microorganisms failed to provide the desired specificity or productivity.

The examples below demonstrate the evaluation of microorganisms in the reduction of this invention and the preparation of milligram quantities of the hydroxy compound of formula I.

EXAMPLE 1

The general method for identifying the stereoselective microbial reduction of the compound of formula II for use as a synthetic precursor for the production of the compound of formula I is described below.

Seed cultures of yeast, filamentous fungi, and bacteria were grown in 125 ml or 300 ml flasks containing 25 ml or 50 ml of YPD (1% yeast extract, 2% peptone, 2% dextrose; pH 5.5), SIM6 (3.5% soy flour, 5% white potato dextrin, 0.5% cerelose, 2 mg/l cobalt chloride, 0.5% calcium carbonate; pH 6.0) and NYC (0.8% nutrient broth, 2% yeast extract, 1.1% cerelose; pH 7.0) media, respectively, for 72 hours at 30° C. with agitation (175–250 rpm) prior to inoculation (4% v/v) into flask fermentations (25 ml YPD/125 ml flask for yeast and filamentous fungi or 25 ml NYC/125 ml flask for bacteria) which were incubated at 30° C. with agitation (250 rpm). In all fermentations, medium pH was adjusted prior to inoculation but was not controlled during culture propagation and ketone reduction. Reduction was initiated by adding 0.5–1.0 g/l of the ketone compound of formula II dissolved in ethanol (25 mg/ml) directly to cultures following 24 hours of growth. Samples of fermentation broth extracted with EtOAc (1:1) following 48 hours incubation with substrate were analyzed by reverse-phase HPLC. Cultures demonstrating consistent reduction activity without significant substrate degradation following repeated fermentations using this procedure were further analyzed by chiral HPLC to determine the configuration of the product alcohol. Cultures capable of reducing the ketone of formula II at 1.0 g/l in high enantiomeric excess yielding the hydroxy compound of formula I the S enantiomer), are summarized in Table 1.

TABLE 1

Microorganisms capable of selectively reducing Compound II to Compound I at 1.0 g/l.

| Culture | Strain # | % EE, S/R | % Yield |
| --- | --- | --- | --- |
| Aspergillus niveus | 12276 | 100 S | 7 |
| Curvularia lunata | 34477 | 100 S | 18 |
| Mucor racemosus | 7924 | 100 S | 4 |
| Mucor circinelloides | 1207a | 100 S | 9 |
| Saccharomyces cerevisiae | Y-2034 | 100 S | 8 |
| Saccharomyces uvarum | 10613 | 100 S | 11 |
|  | 32634 | 100 S | 7 |
| Pichia methanolitica | 58403 | 84 S | 24 |
| Torulaspora fermentati | 20100 | 100 S | 5 |
| Torulaspora species | 66815 | 100 S | 14 |
| Neurospora crassa | 14692 | 76 S | 4 |
| Rhodococcus erythropolis | 25544 | 100 S | 6 |
| Rhodococcus fascians | 202210 | 100 S | 46 |
| Rhodococcus rhodochrous | 999 | 100 S | 12 |
|  | 21243 | 100 S | 12 |
|  | 29670 | 100 S | 13 |
|  | 29675 | 100 S | 8 |
| Rhodococcus species | 19071 | 100 S | 10 |
|  | 19148 | 100 S | 8 |
| Geotrichum candidum | 74487 | 100 S | 25 |
| Doratomyces stemonitis | SPR 423 | 100 S | 11 |
| Scytalidium lignacola | SPR 531 | 89 S | 30 |
| Mortierella isabellina | SPR 875 | 57 S | 35 |

*ATCC accession number to be determined.

EXAMPLE 2

The general method for investigating the fermentation parameters for the reduction of the ketone compound of formula II by *Rhodococcus fascians* ATCC No. 12975 or fungal isolate *Geotrichum candidum* ATCC No. 74487 capable of reducing compound II at concentrations greater than those used in Example 1 is described below.

Seed culture propagation and bioconversions employing *Rhodococcus fascians* ATCC No. 202210 and *Geotrichum candidum* ATCC No. 74487 were conducted in 125 ml flasks containing 25 ml of NYC, YPD, SIM6 or TGP (1% Tastone 154, 2% glycerol, 1% potassium phosphate dibasic, pH 7.0) media for 24–72 hours at 30° C. with agitation (250 rpm) prior to inoculation (4% v/v) into 125 ml flasks containing 25 ml of bioconversion media as summarized in Tables 2 and 3. In all fermentations, medium pH was adjusted prior to inoculation but was not controlled during culture propagation and ketone reduction. Reduction was initiated by adding ketone compound of formula II at 1–10 g/l dissolved in ethanol or dimethyl sulfoxide (DMSO) (25–50 mg/ml) directly to cultures following 24–48 hours of growth. In bioconversions using cell concentrates, cultures were isolated by centrifugation (8000 rpm×10 min.) following 24–48 hours of growth and resuspended in fresh media as indicated prior to the addition of ketone. Samples of fermentation broth extracted with EtOAc (1:1) or TBME (1:1) following 48–96 hours incubation with substrate were analyzed by reverse-phase HPLC to assess yield; analysis by chiral HPLC was conducted to confirm selective synthesis of the S enantiomer product (compound of formula I) in high enantiomeric excess.

TABLE 2

Effect of bioconversion parameters on productivity of R. fascians ATTC No. 202210.

| Seed Propagation conditions: 30° C., 250 rpm | Bioconversion Conditions (25 ml media/125 ml flask, 250 rpm) | % Yield |
|---|---|---|
| 25 ml NYC/125 ml flask | 1 g/l: YPD, 30° C. | 41 |
| 24 hours (4% v/v transfer) | 2 g/l: YPD, 30° C. | 32 |
| 25 ml YPD/125 ml flask | 1 g/l: YPD, 30° C. | 50 |
| 24 hours (4% v/v transfer) | 2 g/l: YPD, 30° C. | 42 |
| 25 ml NYC/125 ml flask | 1 g/l: NYC, 25° C. | 45 |
| 72 hours (4% v/v transfer) | 1 g/l: NYC, 30° C. | 42 |
| | 1 g/l: YPD, 30° C. | 47 |
| | 1 g/l: NYC, 35° C. | 48 |
| | 2 g/l: NYC, 25° C. | 44 |
| | 2 g/l: NYC, 30° C. | 43 |
| | 2 g/: YPD, 30° C. | 44 |
| | 2 g/l: NYC, 35° C. | 39 |
| 25 ml TGP/125 ml flask | 1 g/l: TGP, 30° C. | 69 |
| 24 hours (4% v/v transfer) | 2 g/l: TGP, 30° C. | 64 |
| | 4 g/l: TGP, 30° C. | 28 |
| | 10 g/l: TGP, 30° C. | 11 |
| 25 ml TGP/125 ml flask | 4 g/l: 5× cell concentrate, TGP, 30° C. | 68 |
| 24 hours (4% v/v transfer) | 10 g/l: 5× cell concentrate, TGP, 30° C. | 31 |

Ketone compound of formula II dissolved in ethanol (25–50 mg/ml) added at 1–10 g/l where indicated following 24 hours of growth.

TABLE 3

Effect of bioconversion parameters on productivity of G. candidum ATCC No. 74487.

| Seed propagation conditions | Bioconversion Conditions (25 ml media/125 ml flask) | % Yield |
|---|---|---|
| 25 ml SIM-6/125 ml flask, | 2 g/l: TGP, 30° C. | 18 |
| 30° C., 250 rpm | 4 g/l: TGP, 30° C. | 9 |
| 72 hours (4% v/v transfer) | 10 g/l: TGP, 30° C. | 6 |
| | 2 g/l: YPD, 30° C. | 33 |
| | 2 g/l: YPD, 35° C. | 39 |
| | 2 g/l: TNC, 30° C. | 38 |
| | 2 g/l: TNC, 35° C. | 45 |
| | 2 g/l: TN2C, 30° C. | 54 |
| | 2 g/l: TN2C, 35° C. | 46 |

Ketone compound of formula II dissolved in ethanol (25–50 mg/ml) added at 2–0 g/l following 24–48 hours of growth. TNC medium: 1% Tastone 154, 2% NZ-amine, 3% cerelose, pH 5.5. TN2C medium: TNC medium with 6% cerelose.

EXAMPLE 3

Milligram quantities of the hydroxy compound of formula I derived from the stereoselective reduction of ketone compound of formula II were prepared using *Rhodococcus fascians* ATCC No. 202210 and fungal isolate *Geotrichum candidum* ATCC No. 74487 in multiple flask fermentations employing conditions summarized in Tables 2 and 3. Following 72–96 hours of incubation, fermentation broths of each of the cultures were pooled prior to centrifugation to isolate the cells which harbor most of the product and residual substrate. The cell pellets were extracted with TBME (10–20 volumes/wet weight). Anhydrous $MgSO_4$ was added to the TBME extract to remove residual water, the extract was filtered and the filtrate concentrated by evaporation.

Extract concentrate was subjected to purification by preparative thin layer chromatography employing 10–20 GF silica plates (20 cm×20 cm×1000 micron) and developed with a solution of EtOAc:hexane (50:50). Material comigrating with the desired product was scraped from each of the silica plates, pooled and eluted from the silica with TBME which was subsequently evaporated to dryness. Approximately 170 mg of product derived from 450–600 mg of ketone compound of formula II was isolated from each culture bioconversion. Isolated material was confirmed to be the desired hydroxy compound of formula I by reverse phase and chiral HPLC, NMR, and mass spectrum analyses.

What is claimed is:

1. A process for the stereoselective reduction of 1-(4-fluorophenyl)-3(R)-[3-oxo-3-(4-fluorophenyl)propyl)]-4(S)-(4-hydroxyphenyl)-2-azetidinone to 1-(4-fluorophenyl)-3(R)-[3(S)-hydroxy-3-(4-fluorophenyl)-propyl)]-4(S)-(4-hydroxyphenyl)-2-azetidinone comprising adding 1-(4-fluoro-phenyl)-3(R)-[3-oxo-3-(4-fluorophenyl)-propyl)]-4(S)-(4-hydroxyphenyl)-2-azetidinone to a microorganism in medium, medium and buffer, medium and solvent, or medium and a mixture of buffer and solvent, incubating the resulting mixture, and isolating 1-(4-fluorophenyl)-3(R)-[3(S)-hydroxy-3-(4-fluorophenyl)-propyl)]-4(S)-(4-hydroxyphenyl)-2-azetidinone.

2. The process of claim 1 wherein the microorganism is of the genera selected from the group consisting of Aspergillus, Curvularia, Doratomyces, Geotrichum, Mortierella, Mucor, Saccharomyces, Scytalidium, Pichia, Torulaspora, Neurospora and Rhodococcus.

3. The process of claim 2 wherein the microorganism is of the species selected from the group consisting of *Aspergillus niveus, Curvularia lunata, Doratomyces stemonitis, Geotrichum candidum, Mortierella isabellina, Mucor racemosus, Mucor circinelloides, Saccharomyces cerevisiae, Saccharomyces uvarum, Scytalidium lignicola, Pichia methanolitica, Torulaspora fermenti, Neurospora crassa, Rhodococcus erthyropolis, Rhodococcus faciens,* and *Rhodococcus rhodochrous*.

4. The process of claim 3 wherein the microorganism is *Rhodococcus fascians* ATCC No. 202210 or fungal isolate *Geotrichum candidum* ATCC No. 74487.

5. The process of claim 4 wherein the microorganism is *Rhodococcus fascians* ATCC No. 202210.

* * * * *